United States Patent [19]

Gutierrez et al.

[11] Patent Number: 4,771,486
[45] Date of Patent: Sep. 20, 1988

[54] SPUTUM SPECIMEN COLLECTING DEVICE

[76] Inventors: Charles N. Gutierrez, 232 Spring St., Jonesboro, Tenn. 37659; David Vigil, 1245 Isleta Rd., Albuquerque, N. Mex. 87105

[21] Appl. No.: 129,067

[22] Filed: Dec. 7, 1987

[51] Int. Cl.$^4$ ............................................. A61J 19/00
[52] U.S. Cl. .......................................... 4/258; 4/267; 4/283
[58] Field of Search .................. 4/258, 283, 267, 284, 4/317, 318; 232/1, 43.1

[56] References Cited

U.S. PATENT DOCUMENTS

| 753,229 | 3/1904 | Burns et al. | 4/283 |
| 956,407 | 4/1910 | Orszad | 4/283 |
| 1,019,565 | 3/1912 | Walent | 4/283 |
| 1,065,511 | 6/1913 | Edwards | 4/283 X |
| 1,160,553 | 11/1915 | Whalen | 4/283 |
| 2,063,559 | 12/1936 | Rogers | 4/258 |
| 3,629,879 | 12/1971 | Forst | 4/258 |

Primary Examiner—Henry K. Artis

[57] ABSTRACT

A sputum sampling device having capability for sputum-saliva separation, the device comprising a substantially circular cup having a wall portion which tapers inwardly from top to bottom, a separation plate having a substantially elliptical planar confiuration, the major and minor axis of the plate being dimensioned to allow insertion of the plate down into the cup at a slant to position the lower portion of the plate a distance above the bottom of the cup, a plurality of apertures formed in the lower portion of the plate to provide saliva drainage ports, and an upper portion of the plate comprising a roughened textured surface for retracting and holding sputum in position for recovery in order to obtain a sensory and microbiological examination.

5 Claims, 1 Drawing Sheet

SPUTUM SPECIMEN COLLECTING DEVICE

This invention concerns a container for receiving expectorated material wherein the container is provided with novel means for separating and isolating sputum from saliva.

Expectorated sputum is used as they primary specimen to diagnose an array of disease states caused by a multiple set of organisms (pathogens) including *Streptococcus pneumoniae, Haemophilus influenzae, Klebsiella pneumoniae, Pseudomonas aeruginosa, Serratia marcesans, Branhamella catharralis*, and various fungal organisms such as Histoplasma, Blastomyces, Coccidiomyces, *C. albicans*, and *Aspergillus fumigatus*. Also, parasites are often present such as *Stongyloides stercoralis* larvae, especially in immunosuppressed patients who are receiving steroid treatments. All of these organisms are typically found in sputums in diseased states but are usually absent from saliva.

The sputum specimen when received by the microbiology lab is routinely plated on selective media in order to grow and isolate the above organisms and other pathogens as are present and thus achieve a diagnosis. The identified organism is then tested for antibiotic susceptibility if needed.

The isolation of the pathogen in the laboratory is very often hindered by unacceptable specimens which are partially or totally contaminated by saliva and not representative of true sputum.

Saliva is comprised essentially of water and contains small amounts of salts (chlorides, carbonates, phosphates and sulfates), gasses in solution, and abnormal substances such as acetone being excreted by the body. Also found in saliva are organic substances such as enzymes (ptyalin, salivary amylase, maltase and lysozyne), proteins (serum albumin and globulins, mucins) and small amounts of urea, uric acids, creatine and amino acids, and cellular material such as epithelial cells.

Sputum comprises the semi-solid (viscous, purulent, caseous, etc.) substances excreted by coughing or clearing of the throat, and contains a variety of materials from the respiratory tract (trachea and lungs) including cellular debris, mucus, blood, pus, caseous material and microorganisms. The appearance of the sputum and its consistency depends on the underlying conditions, e.g., as follows:

Copious amount—chronic inflamation of bronchial and pulmonary systems;

Scanty amount—pulmonary bronchial acute inflamations and in the early stages of lobar pneumonia and beginning bronchopneumonia;

Color—depends on its origin, cause, and amount of decomposition;

Bronchiectasis—muco-purulent and foul if expectoration is infrequent;

Bronchial asthma—scanty sputum and frothy, later becoming purulent and grayish, containing eosinophils;

Bronchitis—mucus, later purulent and in chronic cases greenish—yellow and thick;

Broncho pneumonia—frothy, mucoid, thin mucopurulent, copious, often with blood or prune juice in color;

Empyema—If accompanied by perforations, the sputum resembles that of pulmonary abcesses;

Gangrene of Lung and putrid Bronchitis—obnoxious odor and is purulent, separates into 3 layers containing pus cells, hematoidin crystals and leukocytes; and Lobar pneumonia—scanty and viscid yellowish to green and somewhat mucopurulent during early stages and in later stages rusty, bloody, tenacious, especially near or soon after crisis.

It is thus apparent that the presence of significant amounts of saliva in the diagnostic specimen prevents proper isolation and quantitation of pathogenic organisms, and impairs visual as well as tactile observation of the actual sputum portion of the specimen and thus renders true sputum sampling more difficult. The end result is diminishment of the accuracy and/or ease of the diagnosis, both sensory and microbiologically. Also, excessive saliva in the sample increases the risk of operator contact with the pathogens during the separation of the sputum's purulent material from saliva elements. This often results in "sputum runaround" where it is not possible to reach the sputum due to the hydrophillic nature of the saliva surrounding the desirable sputum material.

Present sputum sampling devices and techniques are not capable of providing a truly representative specimen from mixed specimens and it is the principal object of the present invention to provide a sputum sampling device which allows essentially immediate sputum isolation and its availability for both sensory and biological examination and patient diagnosis.

This and other objects hereinafter appearing have been attained in accordance with the present invention through a sputum—saliva separation device comprising a substantially circular cup having a wall portion which tapers inwardly from top to bottom, a separation plate having a substantially eliptical planar configuration, the major and minor axis of said plate being diminished to allow insertion of the plate down into the cup at a slant to position the lower portion of the plate a distance above the bottom of the cup, a plurality of apertures formed in said lower portion of said plate to provide saliva drainage ports, and an upper portion of said plate comprising a roughened surface for retracting, retaining, and recovery of selective portions of sputum purulent or caseous material for sensory in-situ or other examination, or for recovery for further examination or analysis such as microbiological testing and physical and chemical evaluation.

In preferred embodiments of the present invention:

the device is disposable and comprised of polyolefin material;

the roughened portion of the separation plate is sandpaper textured polyolefin material;

the separation plate is provided with a saliva sampling port in the upper portion thereof adjacent to the upper edge; and the cup is provided at its top with screw-on threads and a screw-on lid.

The invention will be further understood from the following description and drawing wherein.

Figure 1:
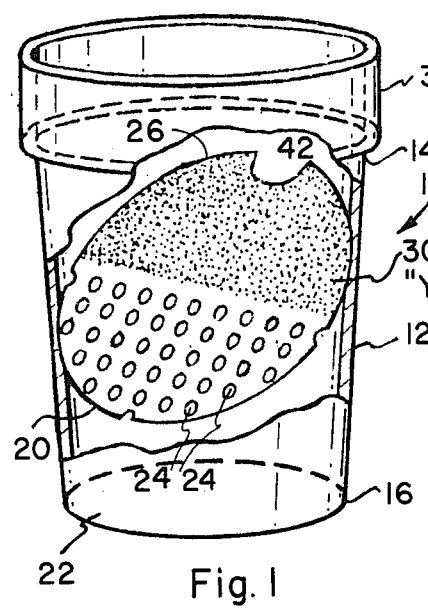
FIG. 1 is a side, isometric view of the present device, with portions of the cup broken away to show the separation plate in operative position.
Figure 2:
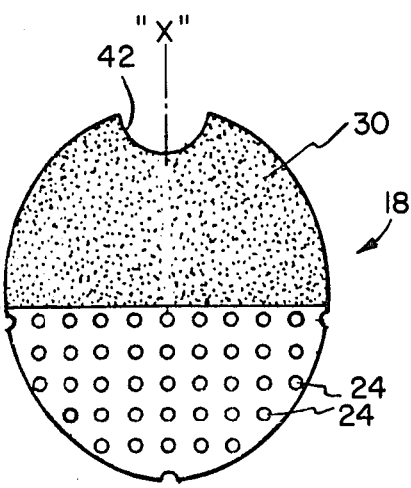
FIG. 2 is a top elevational view of the separation plate.

Referring to the drawing and claims, the present sputum sampling device comprises a substantially circular cup 10 having a wall portion 12 which tapers inwardly from top 14 to bottom 16, a separation plate 18 having a substantially eliptical planar configuration, the major "x" and minor "y" axis of the eliptical plate being dimensioned to allow insertion of the plate down into the cup at a slant to position the lower portion 20 of the plate a distance above the bottom 22 of the cup, a plurality of apertures 24 formed in the lower portion of the plate to provide saliva drainage ports, and an upper portion 26 of the plate comprising a roughened surface 30 for retracting and retaining the sputum's purulent copius material in position for in-situ sensory examination or for recovery for further examination or analysis.

The cup, plate, and cover may be of any material such as plastic (including polyolefin, polyester, polyamide, polycarbonate, polyurethane or the like), metal, or ceramic, with polypropylene or polyethylene being preferred. The degree of taper of the cup wall is not critical but preferably is such as shown in FIG. 1 whereby the plate is readily wedged or fastened into the position shown therein. It is noted that the taper provides a means for positively limiting the extent to which the plate can be inserted into the cup and thus insure a saliva sump at the bottom of the cup which is adequate to isolate saliva from sputum.

Figure 4:
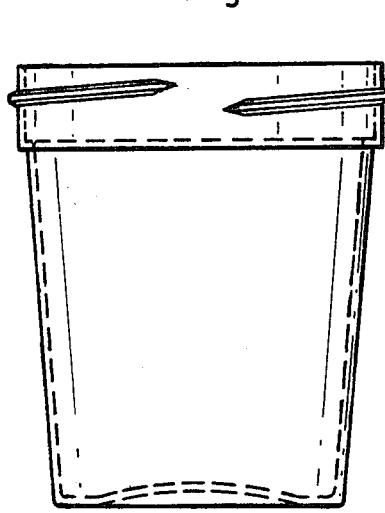
FIG. 4 is a side elevational view of a preferred cup structure with portions shown in section.
Figure 3:
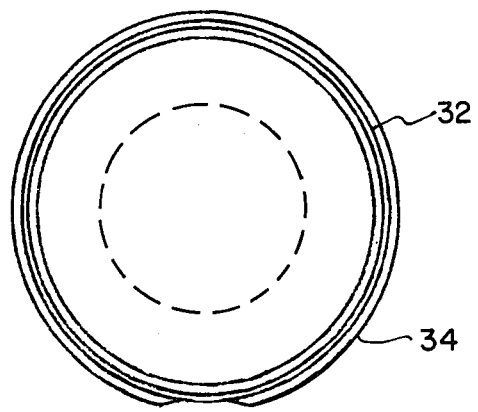
FIG. 3 is a side elevational view of the separation plate.
Figure 5:
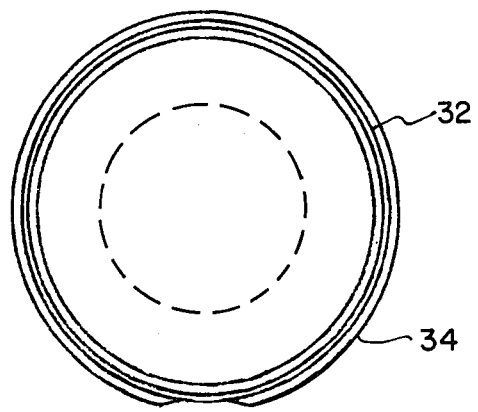
FIG. 5 is a top elevational view of the cup structure of FIG. 4.
Figure 6:
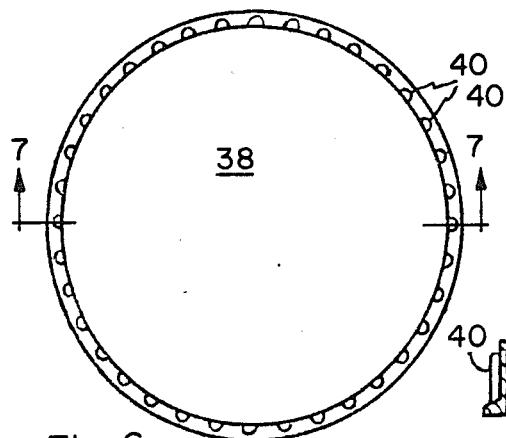
FIG. 6 is a top elevational view of a preferred cover.
Figure 7:
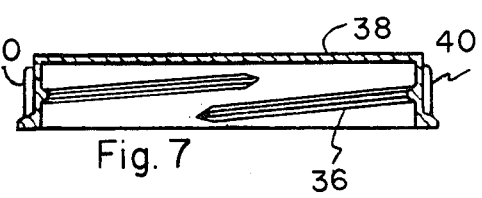
FIG. 7 is a cross-sectional view taken along line 7—7 of FIG. 6 in the direction of the arrows.

The cup may be provided with an upper rim 32 and a screw thread 34 as shown in FIGS. 4 and 5 for receiving the mating thread 36 of a cover or lid 38 shown in FIGS. 6 and 7. The lid is provided, preferably, with peripheral ridges 40 for ease of gripping.

Plate 18 is dimensioned along its major and minor axis to allow wedging or fastening of the plate at approximately the position shown in FIG. 1 wherein the plate is slanted to the horizontal, between about 28° and about 34°. This angle may be widely varied, e.g., between about 20° and about 40°. The roughened surface 30 of the plate consists of sandpaper texture or the like, and may be formed, e.g., by the molding operation, onto the surface of the plate. A cut-out or port 42, preferably of approximately a 5/16 in. radius, is preferably provided in the upper portion of the plate to allow the insertion therethrough of a Dacron swab, pipet, or the like for extracting a test sample of the saliva or other substance which has drained through ports 24 into the bottom of the cup.

In using the present device, the expectoration is made into the cup, either on the side wall or onto the plate, whereby the saliva will drain through ports 24 while the sputum's purulent and copius materials will remain on top or float to the bottom portion to be trapped on the plate. Sensory examination of the sputum is made by coaxing it upwards on the plate onto the roughened portion 30 with a suitable instrument preferrably a Dacron swab, where the purulent material is frictionally retained or removed for inspection. It is noted that the size of the cup parts and the size of ports 24 may be extensively varied, however, the relative dimensions as shown in the drawing are highly acceptable. Typical port diameters range, e.g., from about 1/32 to about 3/16 inch. In this regard, the plate itself may be made of a fairly rigid wire mesh or comparable sieve-like material including Nylon mesh fabric, to which the roughened portion 30 is attached by any suitable means.

The invention has been described in detail with particular reference to preferred embodiments thereof, but it will be understood that variations and modifications will be effected within the spirit and scope of the invention.

I claim:

1. A sputum sampling device having capability for sputum saliva separation, said device comprising a substantially circular cup having a wall portion which tapers inwardly from top to bottom, a separation plate having a substantially eliptical planar configuration, the major and minor axis of said plate being dimensioned to allow insertion of the plate down into the cup at a slant to position the lower portion of the plate a distance above the bottom of the cup, a plurality of apertures formed in said lower portion of said plate to provide saliva drainage ports, and an upper portion of said plate comprising a roughened surface for holding the sputum's purulent or copius material in position for sensory examination or recovery.

2. The device of claim 1 comprised of polyolefin material.

3. The device of claim 1 wherein the roughened portion of the plate is a molded sandpaper textured surface.

4. The device of claim 1 wherein a saliva sampling port is provided in the upper portion of the plate adjacent the edge thereof.

5. The device of claim 1 provided with a screw-on lid.

* * * * *